(12) United States Patent
Skubal et al.

(10) Patent No.: US 7,914,736 B2
(45) Date of Patent: Mar. 29, 2011

(54) SEMICONDUCTOR-BASED DETECTION AND DECONTAMINATION SYSTEM

(75) Inventors: Laura R. Skubal, West Brooklyn, IL (US); Alan L. McArthur, Mokena, IL (US)

(73) Assignee: Uchicago Argonne, LLC, Chicago, IL (US)

( * ) Notice: Subject to any disclaimer, the term of this patent is extended or adjusted under 35 U.S.C. 154(b) by 193 days.

(21) Appl. No.: 11/443,955

(22) Filed: May 31, 2006

(65) Prior Publication Data
US 2007/0280852 A1 Dec. 6, 2007

(51) Int. Cl.
*G01N 31/00* (2006.01)
*G01N 30/96* (2006.01)
*G01J 1/48* (2006.01)

(52) U.S. Cl. ............... 422/62; 422/86; 422/88
(58) Field of Classification Search ................ 422/3, 22, 422/62, 4, 86, 88
See application file for complete search history.

(56) References Cited

U.S. PATENT DOCUMENTS

| | | | |
|---|---|---|---|
| 5,275,957 A | 1/1994 | Blades et al. | |
| 5,448,906 A | 9/1995 | Cheung | |
| 5,525,520 A | 6/1996 | Dinh | |
| 5,989,990 A | 11/1999 | Koh et al. | |
| 6,108,476 A | 8/2000 | Iimura | 385/128 |
| 6,203,678 B1 | 3/2001 | Leonhard et al. | |
| 6,235,351 B1 | 5/2001 | DiMarzo et al. | 427/453 |
| 6,501,893 B1 | 12/2002 | Iimura | 385/128 |
| 6,634,210 B1 * | 10/2003 | Bosch et al. | 73/23.33 |
| 6,771,866 B2 | 8/2004 | Iimura | 385/128 |
| 6,783,740 B2 * | 8/2004 | Colby et al. | 422/186.3 |
| 7,394,118 B2 * | 7/2008 | Zhou | 257/253 |
| 7,510,470 B2 * | 3/2009 | Arts | 454/187 |
| 2004/0161949 A1 * | 8/2004 | Yadav et al. | 438/800 |
| 2006/0154414 A1 * | 7/2006 | Lin | 438/222 |
| 2006/0210421 A1 * | 9/2006 | Hammond et al. | 422/3 |

OTHER PUBLICATIONS

*Chemical Engineering Science*, vol. 56, 1561 (2001).
L.R. Skubal, et al., "Detection and identification of gaseous organics using $TiO_2$ sensor," *Journal of Photochemistry and Photobiology A: Chemisty* 148, 103-108 (2001).
A. Rothschild, et al. "Sensing Behavior of $TiO_2$ Thin Films Exposed to Air at Low Temperatures," *Sensors and Actuators B*, vol. 67, 282 (2000).
R. K. Sharma, et al., "Influence of Doping on Sensitivity and Response Time of TiO2 Oxygen Gas Sensor," *Review of Scientific Instruments*, vol. 71, 1500 (2000).
N. Golego, et al., "Sensor Phtoresponse of Thin-Film Oxides of Zinc and Titanium to Oxygen Gas," *J. Electrochem. Soc.*, vol. 147, 1592 (2000).

(Continued)

*Primary Examiner* — Sean E Conley
*Assistant Examiner* — Kevin C Joyner
(74) *Attorney, Agent, or Firm* — Cherskov & Flaynik

(57) ABSTRACT

A system and method for identifying and making quantitative determinations of different deposits on a portion thereof, determining that the deposit is a contaminant and decontaminating at least the portion of the system is disclosed. The system comprises a controller, a sensing portion and a decontamination portion. The controller contains information about at least one noncontaminant. The sensing portion communicates with at least the controller and the portion of the system and is adapted to detect the deposit. The decontaminating portion communicates with at least the controller and is adapted to decontaminate the portion of the system.

13 Claims, 15 Drawing Sheets

OTHER PUBLICATIONS

G. Sbeerveglieri, et al., "Titamium Dioxide Thin Films Prepared for Alcohol Microsensor Applications," *Sensors and Actuators B*, vol. 66, 139 (2000).

M. R. Islam, et al., "Chemical Sensor Based on Titanium Dioxide Thick Film: Enhacement of Selectivity by Surface Coating," *Appl. Surface Sci.*, vol. 142, 262 (1999).

N. Kumazawa, et al., "Photoresponse of a Titanium Dioxide Chemical Sensor," *J. Electro. Chemistry*, vol. 472, 137 (1999).

* cited by examiner

SEMICONDUCTOR-BASED DETECTION AND DECONTAMINATION SYSTEM

CONTRACTUAL ORIGIN OF THE INVENTION

The United States Government has rights in this invention pursuant to Contract No.: W-31-109-39-ENG between the Government and the University of Chicago representing Argonne National Laboratory.

BACKGROUND OF THE INVENTION

1. Field of the Invention

Embodiments of the present invention relate generally to a detection and decontamination system and method. More specifically, embodiments of the present invention relate to a system and method for rapidly and accurately detecting, characterizing, quantifying, and decontaminating organics present in the atmosphere due to chemical and/or biological spills, weapons, terrorist attack and/or other releases.

2. Background of the Invention

In the event of a chemical and/or biological spill, weapon, terrorist attack and/or release, rapid detection, characterization, quantification, and decontamination is crucial. Commercially available sensors and sensing technologies provide for detecting contaminants on the surface of an object. However, these sensors and technologies generally require collecting a sample of the contaminant which must then be transported to a remote instrument for contaminant identification and concentration determination.

Photocatalytic agents are effective for removing organic pollutants in both aqueous and gaseous environments. Heterogeneous semiconductor photocatalysis relies upon photoactive semiconductors, such as titanium dioxide ($TiO_2$) for example, to not only sorb noxious and pollutant gaseous emissions, but to photocatalyticaly oxidize or reduce such emissions into less toxic organics and carbon dioxide.

As illustrated in Equation 1 below, when $TiO_2$ is illuminated by light having energy hv equal to or exceeding the $TiO_2$'s bandgap energy (3.2 electron volts for anatase $TiO_2$), electrons (e−) are excited (promoted) into the conduction band. Electron promotion creates positive holes ($h^+$) in the valence band. If these electron-hole pairs do not recombine to produce heat (as illustrated in Equation 2 below), the pairs promote oxidative and reductive electron transfers as shown in Equations 3 through 7 (adapted from *Chemical Engineering Science*, Vol. 56, 1561 [2001]).

| | |
|---|---|
| Eq. 1 $TiO_2 + hv \rightarrow TiO_2 (h^+ + e^-)$ | electron-hole pair formation |
| Eq. 2 $e^- + h^+ \rightarrow$ heat | recombination |
| Eq. 3 $e^- + M^{n+} \rightarrow Mn^{(n-1)+}$ | reduction |
| Eq. 4 $h^+ + H_2O_{(ads)} \rightarrow {}^\bullet OH + H^+$ | oxidation of adsorbed (abs) water |
| Eq. 5 $h^+ + 2OH^-_{(ads)} \rightarrow {}^\bullet OH + OH^-$ | oxidation of adsorbed hydroxide ions |
| Eq. 6 ${}^\bullet OH + R_{(ads)} \rightarrow {}^\bullet R_{(ads)} + H_2O$ | organic oxidation |
| Eq. 7 ${}^\bullet R + ({}^\bullet OH, {}^\bullet R_{ads}) \rightarrow$ products | termination | where hv=light energy, $h^+$=positive holes, $e^-$=electrons, $M^{n+}$=oxidized compound and $R_{(abs)}$=the absorbed organic species or moiety.

The charges in the valence and conduction bands can oxidize and reduce moieties at the $TiO_2$ surface. In addition, the positive holes often react with water or hydroxyl ions sorbed to $TiO_2$, producing hydroxide radicals which, in turn, oxidize absorbed organic moieties.

$TiO_2$ has been found to be an effective oxygen sensor, since the oxygen diffuses into $TiO_2$ oxygen vacancies, thus increasing the $TiO_2$ resistivity. This is especially true at elevated temperatures. See, for example, A. Rothschild, et al. "Sensing Behavior of $TiO_2$ Thin Films Exposed to Air at Low Temperatures," *Sensors and Actuators B*, Vol. 67, 282 (2000); R. K. Sharma, et al., "Influence of Doping on Sensitivity and Response Time of $TiO_2$ Oxygen Gas Sensor," *Review of Scientific Instruments*, Vol. 71, 1500 (2000); and N. Golego, et al., "Sensor Photoresponse of Thin-Film Oxides of Zinc and Titanium to Oxygen Gas," *J. Electrochem. Soc.*, Vol. 147, 1592 (2000).

$TiO_2$ thin films have been used, at elevated temperatures (100° C. to 500° C.), to detect different types of alcohols including ethanol, methanol and propanol. See, for example, G. Sbeerveglieri, et al., "Titanium Dioxide Thin Films Prepared for Alcohol Microsensor Applications," *Sensors and Actuators B*, Vol. 66, 139 (2000).

Resistivity changes occur when gases chemisorb onto the $TiO_2$ surface. Such resistivity changes have been used to derive current, phase lag, and surface potential interactions, producing one-point relationships unique to the individual compounds sorbed onto the $TiO_2$. See, for example, M. R. Islam, et al., "Chemical Sensor Based on Titanium Dioxide Thick Film: Enhancement of Selectivity by Surface Coating," *Appl. Surface Sci.*, Vol. 142, 262 (1999).

The chemisorption of compounds onto the $TiO_2$ surface has also been used to capture distinct responses from applied sinusoidal voltages on rutile $TiO_2$ films in the presence of various organic gases. These responses were enhanced in the presence of 700 nanometer (nm) light. See, for example, N. Kumazawa, et al., "Photoresponse of a Titanium Dioxide Chemical Sensor," *J. Electro. Chemistry*, Vol. 472, 137 (1999).

U.S. Pat. No. 6,203,678 issued on Mar. 20, 2001 to Leonhard, et al. discloses a galvanic solid electrolyte sensor for measuring gaseous anhydrides. The sensor includes a ceramic solid electrolyte, a measuring electrode, and a spatially separated reference electrode.

U.S. Pat. No. 5,989,990 issued on Nov. 23, 1999 to Koh, et al., discloses a method for fabricating a tin oxide thin-film sensor using an ion cluster beam deposition ("ICBD") process.

U.S. Pat. No. 5,525,520 issued on Jun. 11, 1996 to Dinh, discloses a photoactivated, light emitting luminescence sensor and method of detecting trichloroethylene and related volatile organochloride compounds wherein the compounds are directly dissociated by light.

U.S. Pat. No. 5,448,906 issued on Sep. 12, 1995 to Cheung, discloses an ambient temperature, solid state, tin oxide (SnO), or zinc oxide (ZnO) sensor for the detection of oxygen which relies solely upon sorption/desorption.

U.S. Pat. No. 5,275,957 issued on Jan. 4, 1994 to Blades, et al., discloses a method for using $TiO_2$'s photocatalytic properties to enhance the disintegration rates of organics in waters.

None of the aforementioned references, however, discloses detecting a deposit, making quantitative determinations with respect to the deposit (i.e., identifying a contaminant and the quantity), "self"-decontaminating the deposit, and determining when chemical decontamination/neutralization is complete.

A need exists in the art for a device and method to detect a substance, make quantitative measurements regarding the substance, detoxify or alter the substance, and indicate when substance (toxic) neutralization is complete. The device and method should perform these functions in real-time or near real-time, so as to facilitate in-situ triage decisions at contaminated sites.

SUMMARY OF THE INVENTION

It is an object of the present invention to provide a surface and method for detecting a deposit of a substance, making quantitative determinations with respect to the deposit (i.e., identifying a contaminant and the quantity) and decontaminating the deposit which overcomes many of the disadvantages of the prior art.

Another object of the present invention is to provide a surface to facilitate rapid detection and detoxification of a moiety contacting the surface. A feature of the surface is the utilization of various exited states of semiconductors comprising the surface to determine the presence, quantity and alteration of the moiety. An advantage of the surface is that the aforementioned determination occurs upon excitation of the semiconductor.

Embodiments of the present invention relate to a detection and decontamination system and method for identifying and making quantitative determinations with respect to different deposits and contaminants (gaseous organic moieties for example). More specifically, embodiments of the present invention relate to a system and method for detecting, characterizing, quantifying and decontaminating chemical and biological spills, releases or weapons.

In the event of a spill, terrorist attack, or other chemical and/or biological release, it is critical to be able to rapidly detect the components that have been released, determine the concentration of the components, decontaminate the released components, and verify that the decontamination efforts have been successful.

Embodiments of the invention include a "smart" surface that may be incorporated into fabrics, painted surfaces, etc. and used by the military for fast response and decontamination in combat situations or by the government in subway systems, air ventilation systems, and for other large surface areas that may require decontamination. The smart surfaces can constantly monitor the atmosphere above them, and, if contamination occurs in the proximity of the smart surface, a signal is triggered that identifies the constituent and concentration, and initiates self decontamination of the surface.

The smart surface system comprises a controller, a sensing portion and a decontamination portion. The controller contains information about the uncontaminated surface and at least one contaminant. The sensing portion communicates with at least the controller and the decontamination portion of the system and is adapted to detect the deposit. The decontaminating portion communicates with at least the controller and is adapted to decontaminate at least a portion of the affected surface.

A method for identifying and making quantitative determinations with respect to a deposit on at least a portion of a surface also is provided. The method comprises sensing the deposit on the portion of the surface and initiating decontamination of at least the portion of the surface in near real-time. The method further comprises determining if the decontamination of at least the portion of the surface is complete. When complete, the method comprises terminating the decontamination procedure.

Still another embodiment relates to a method for identifying and making quantitative determinations with respect to deposits on at least a portion of a surface. This embodiment of the method comprises determining if the portion of the system is contaminated using an embedded sensing portion. Decontamination of at least the portion of the system is initiated using an embedded decontamination portion. The method further comprises determining if the portion is still decontaminated using the embedded sensing portion; and terminating decontamination of the portion.

These and other objects of the present invention, as well as the advantages thereof, will become clearer from the description which follows.

DESCRIPTION OF THE DRAWING

Embodiments together with the above and other objects and advantages may best be understood from the following detailed description of the embodiments illustrated in the drawings, wherein.

DETAILED DESCRIPTION OF THE INVENTION

In the event of a spill, terrorist attack, or other chemical and/or biological release, it is critical to rapidly detect the components that have been released, their concentrations, decontaminate the released components, and determine whether decontamination efforts have been successful. Embodiments of the present invention relate to a system and method adapted to detect the presence of a deposit (i.e., a contaminant), determine what deposit is present and its concentration, and, in many instances, neutralize (detoxify) the deposit if it is a contaminant, and provide feedback that the deposit is neutralized.

Figure 1:
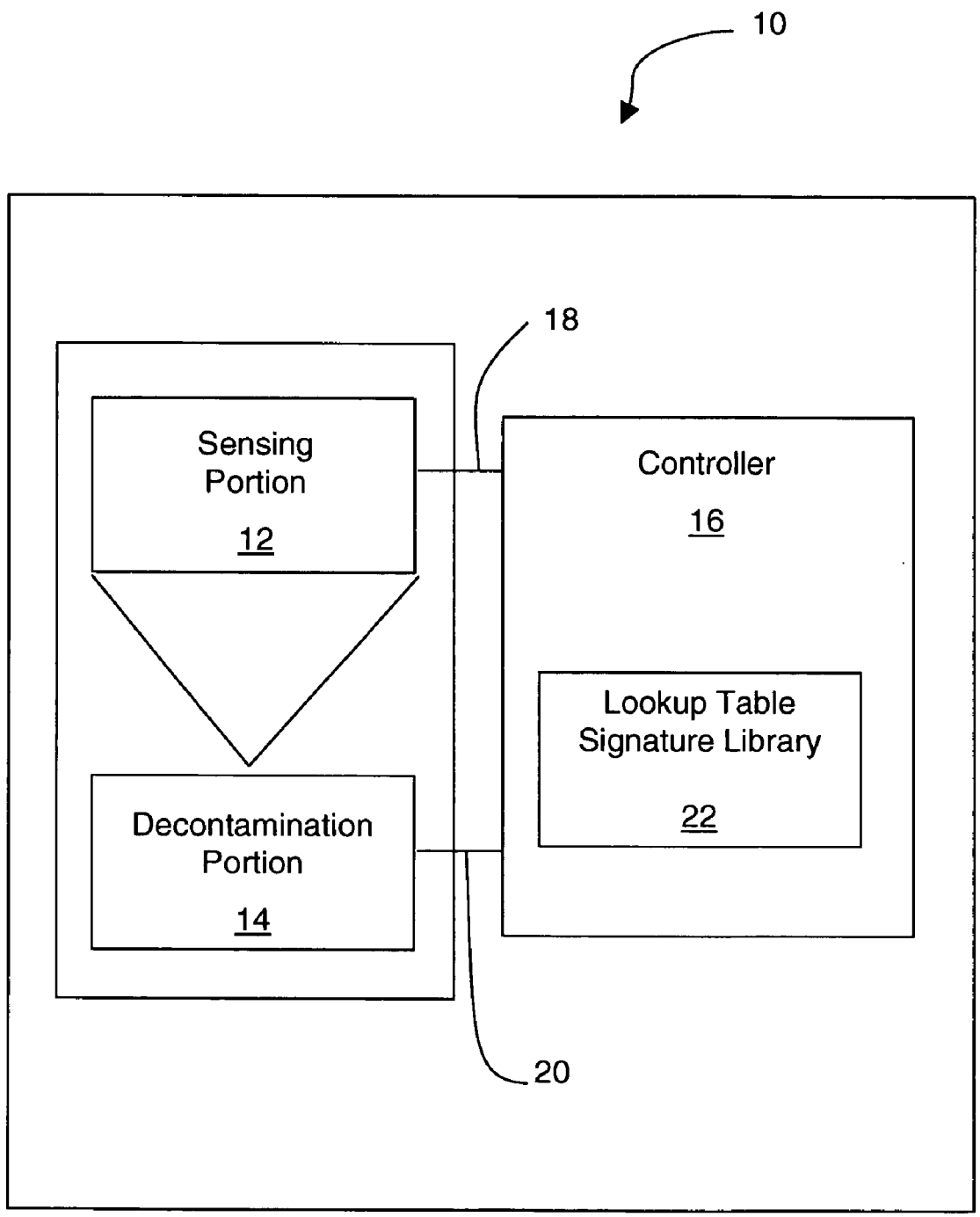
FIG. 1 depicts a block diagram of a detection and decontamination system, in accordance with one embodiment of the present invention.

FIG. 1 depicts a block diagram illustrating a detection and decontamination system (alternatively referred to as "detection/decontamination system" or "system"), generally designated 10, in accordance with one embodiment of the present invention. In the depicted embodiment, the detection/decontamination system 10 comprises an embedded contamination sensing means or portion 12 and an embedded decontamination means or portion 14 coupled to and communicating with a controller 16. The "embedded" feature is meant to designate that a mechanism extends below a visible surface of a substrate, or is substantially encapsulated within the substrate.

In the illustrated embodiment, the sensing and decontamination portions 12, 14 are shown coupled to the controller 16 via connections or coupling means 18 and 20 respectively. In one embodiment, connection 18 comprises one or more wires or cable, while connection 20 comprises one or more fiber optic cables. Other embodiments are contemplated in which the sensing and decontamination portions 12, 14 wirelessly communicate with the controller 16.

In the illustrated embodiment, controller 16 may comprise a microprocessor or microcontroller. The controller 16 contains a buffer or other storage device 22 including a "lookup table" or "signature library." The table/library 22 contains the background resistances at specific temperatures of uncontaminated materials stored as a standard curve.

Figure 2A:
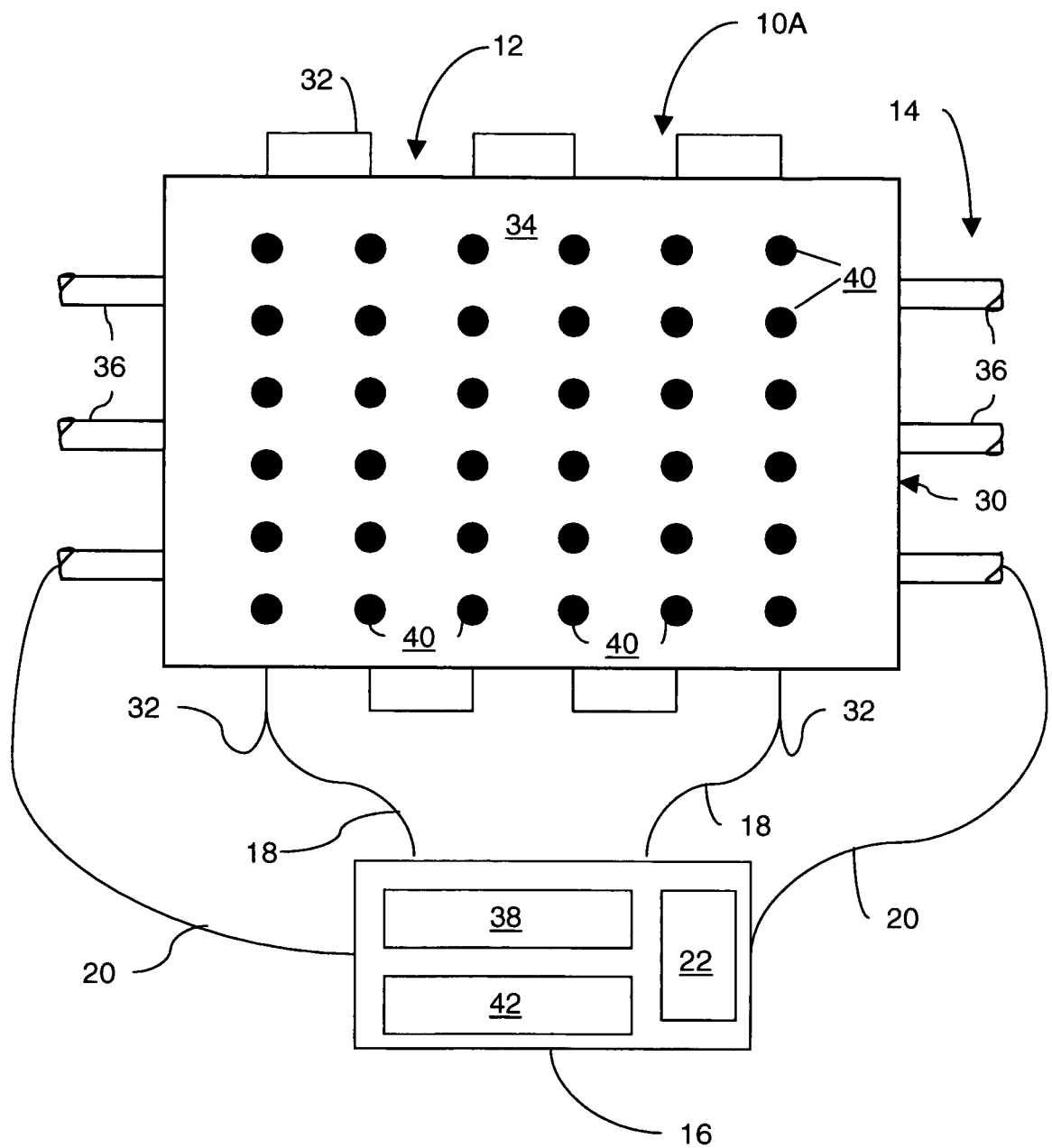
FIGS. 2A & 2B depict schematic representations of the detection and decontamination system of FIG. 1 in accordance with one embodiment of the present invention.
Figure 2B:
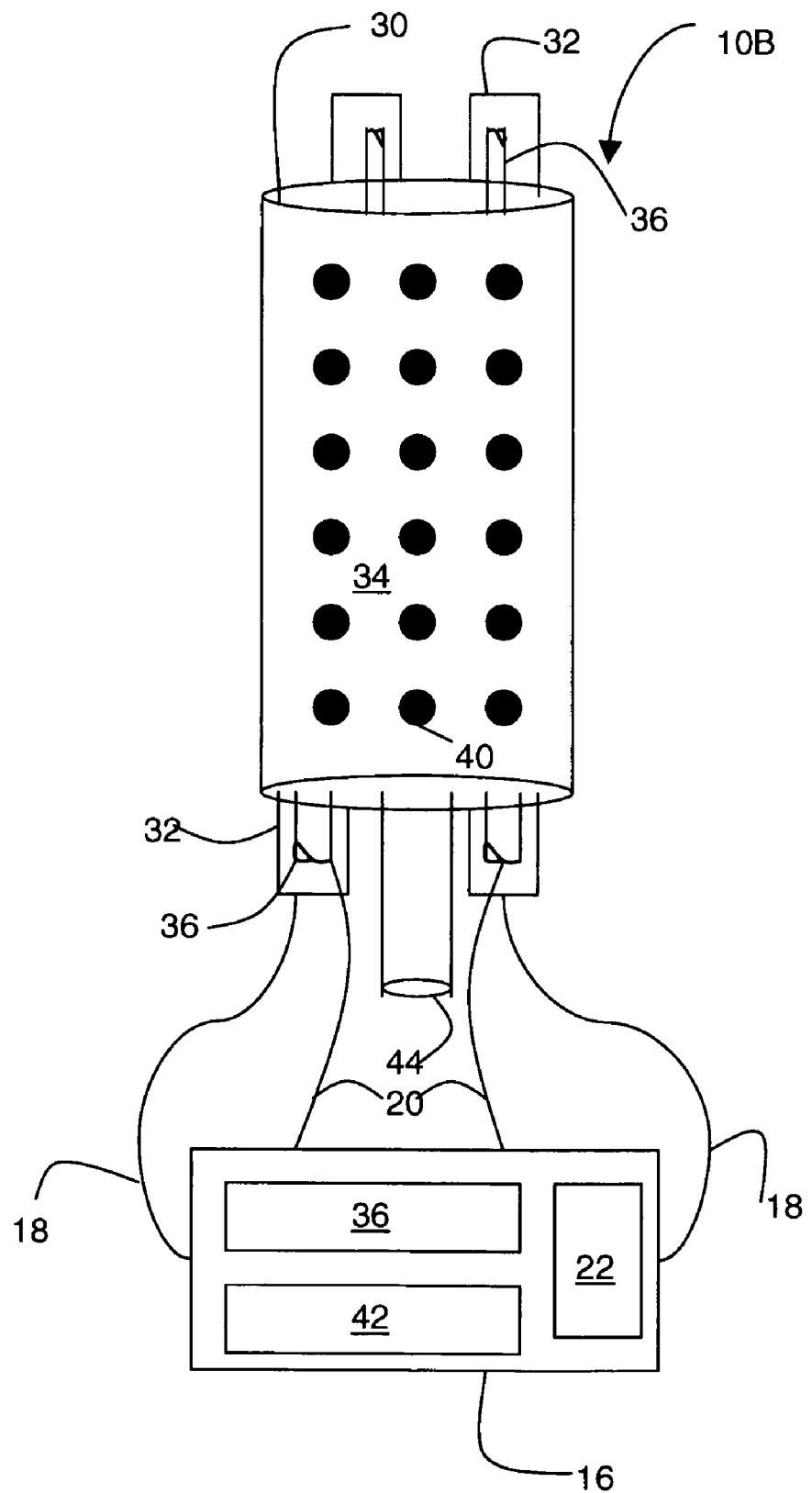

FIGS. 2A and 2B depict alternate embodiments of the system 10. Embodiments of the present invention employ one or more thin films of a semiconductor ($TiO_2$ for example); light having wavelengths more energetic than the semiconductor's bandgap (388 nm light for $TiO_2$, sunlight, xenon light, and mercury lamps, for example) that can be carried by fiber optics to the system or be positioned above the sensing surface; and microelectrodes to detect contaminants and to initiate self-decontamination of the system. More specifically, embodiments comprise conductive films or mesh layers of microcircuits and scored fiber optics embedded in a substrate (including but not limited to glass, ceramics, fabrics, painted surfaces, etc.).

FIG. 2A depicts system 10A (similar to system 10 in FIG. 1) comprising a substrate or surface 30 (here depicted as a portion of a larger surface). The sensing portion 12 comprises microelectrodes, conductive films (thin films for example), and/or one or more mesh layers of microcircuits 32 (alternatively referred to as "electrodes") and one or more semiconductor layers 34 ($TiO_2$ for example). In this embodiment, the decontamination portion 14 comprises one or more microelectrodes, conductive films, semiconductor layers, and scored or unscored fiber optics 36 (alternatively referred to as "optics") to transmit light to the semiconductor layers.

In at least one embodiment, the electrodes 32 are embedded in the substrate 30 and are coupled to and communicate with the controller 16 via one or more connections 18. In the illustrated embodiment, the controller 16 includes an electrode source 38. The electrode 32 periodically or continuously captures or measures at least the resistance of the coated surface 30. This information is transported or transferred to the controller 16 via connections 18, where the information is compared to known background resistance in the table/library 22 in near real-time. In at least one embodiment, the electrodes 32 are adapted to measure the resistance and temperature of the surface 30 and transmit this information to the controller 16.

In the illustrated embodiment, the one or more semiconductor layers include one or more particles 40 of the semiconductor material 34. The particles 40 may comprise macroparticles, microparticles, or nanoparticles, or some combination thereof, of the semiconductor material. In one or more embodiments, the semi-conductor comprises a metal oxide semiconductor (titanium dioxide [$TiO_2$] for example) although other metal oxide semiconductors ($SrTiO_3$, $ZnO$, $SrO$, $In_2O_3$, $GeO_2$, $Nb_2O_5$, $MoO_3$, $CeO_2$, $ThO_2$, $SnO_2$, $ZrO_2$, $VO_2$, $WO_3$, $CdS$, and $Fe_2O_3$ for example) are contemplated.

FIG. 2A further illustrates the controller 16 coupled to optics 36 which transmit light in the ultraviolet spectrum via one or more connections 20. Like the electrodes 32, in one embodiment the optics 36 are embedded in the substrate 30. Further, the optics 36 are adapted to transmit light having a shorter wavelength than the semiconductor's bandgap energy and (sunlight, xenon light, mercury lamps for example). The transmitted light initiates the reaction between the semiconductor and the sorbed contaminant, allowing for self-decontamination (via oxidation or reduction) to occur. In one embodiment, the controller 16 includes a light source 42 adapted to generate light having a wavelength more energetic than (i.e., equal to or exceeding) the semiconductor's bandgap energy (for example, 388 nm for $TiO_2$). However, it also is contemplated that optics 36 transmitting the light are only activated by the source 42.

In operation, a chemical moiety becomes physisorbed or chemisorbed to the surface 30. This physisorbtion or chemisorbtion changes at least the surface resistance (or surface resistance and temperature) of the layers 34 and/or particles 40 as measured by the electrodes 32. The system measures the resistance and temperature. Data representative of the measured resistance and temperature is compared to data containing the background resistances and temperatures of uncontaminated surface materials stored as a standard curve in the look-up table/library 22.

The measured changes trigger a feedback loop that: (1) indicates the surface 30 is contaminated (i.e., the deposit is a contaminant); (2) proposes which moiety is present and the concentration thereof; (3) triggers the illumination of a light at the source 42, which is dispersed throughout the surface via the optics 36 (or alternatively triggers a light source above the surface that illuminates the sensing surface [inducing $TiO_2$ or semiconductor photocatalytic oxidation or reduction of the contaminant]); and (4) provides feedback to the controller 16 as to when the measured resistance matches the stored background resistance, indicating that the contaminant has been oxidized or reduced (decontaminated) and desorbed from the surface 30.

FIG. 2B depicts a system 10B (similar to systems 10 and 10A of FIGS. 1 and 2A). However, in this embodiment the system 10B comprises a wand having a handle 44. It is contemplated that in at least one embodiment, rather than having a fixed system part of a permanent fixture, the system 10B may be mobile. That is, system 10B may be used by an operator as a mobile detection device to sense a contaminant and decontaminate an atmosphere.

Figure 3:
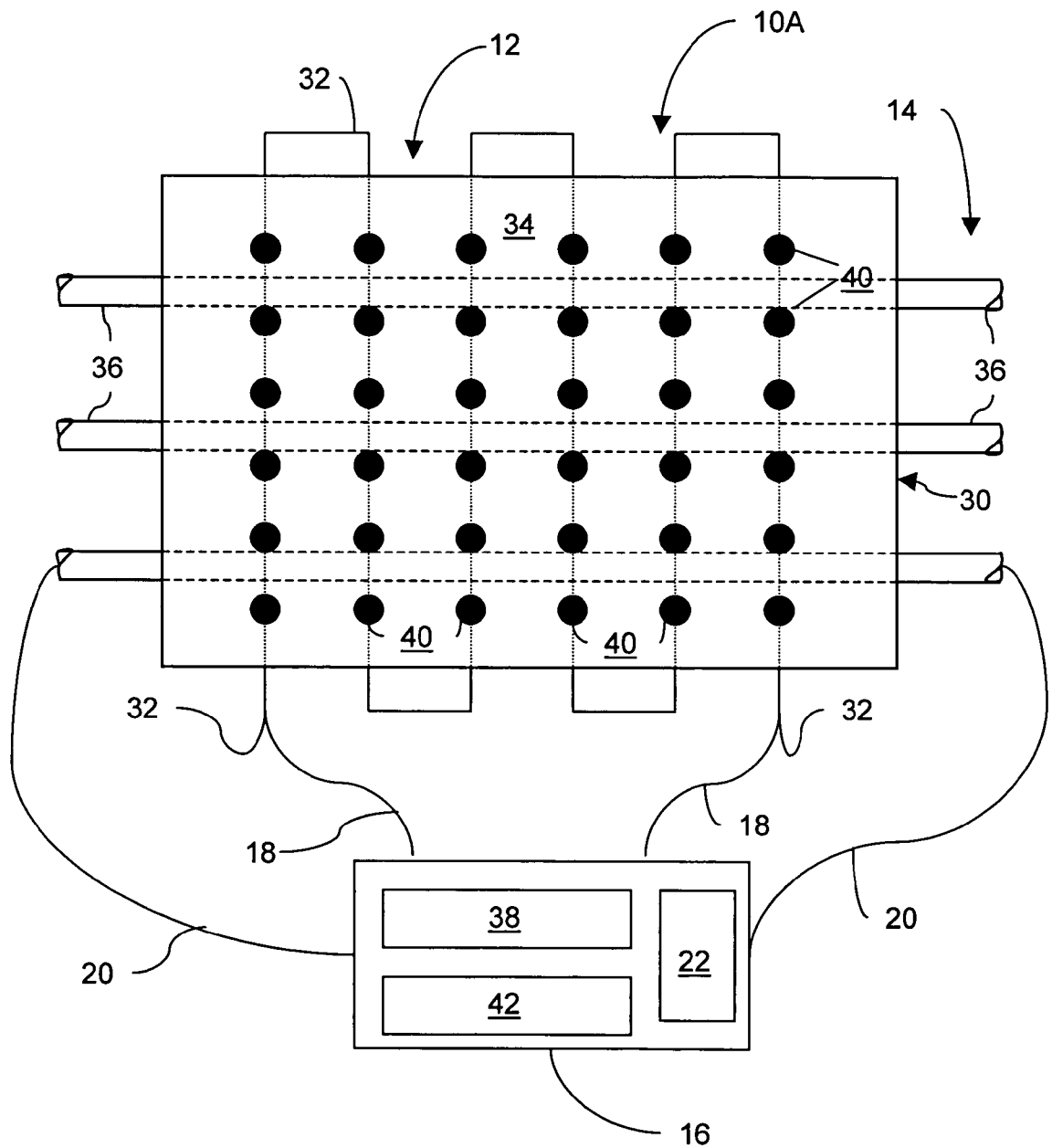
FIG. 3 depicts a plan view of the detection and decontamination system of FIG. 2A illustrating the detecting and sensing portions in dashed lines in accordance with one embodiment of the present invention.

FIG. 3 depicts a plan view of the detection and decontamination system 10A of FIG. 2A. In this embodiment, dashed lines are used to indicate the sensing and decontamination portions 12 and 14. More particularly, the dashed lines indicate the optics 36 are positioned substantially perpendicular to the electrodes 32. Optics, however, also can be positioned in alternative angles and configurations to the surface.

Figure 4:
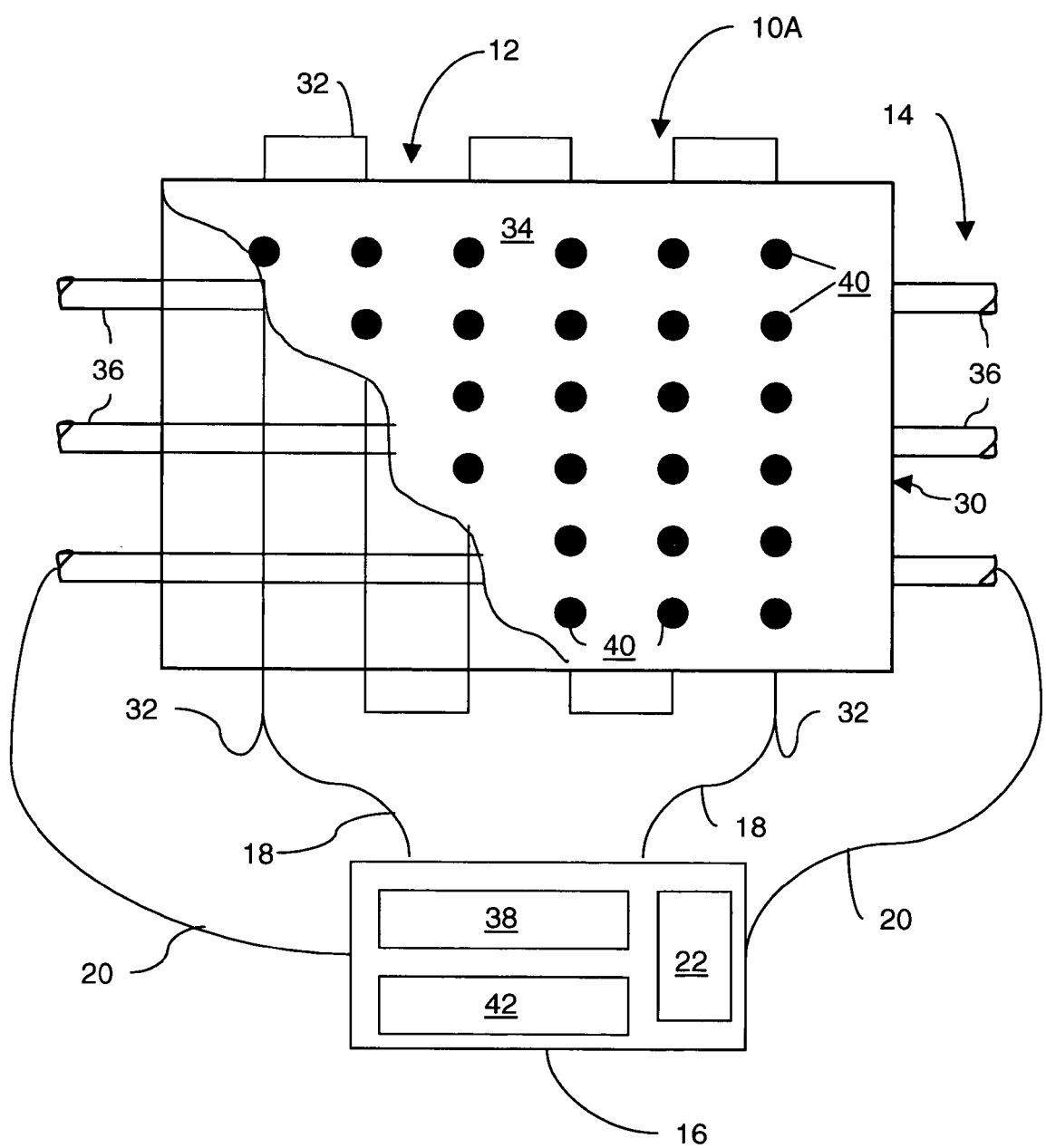
FIG. 4 depicts a plan view in partial cross section of the detection and decontamination system of FIG. 3 in accordance with one embodiment of the present invention.

FIG. 4 depicts a plan view in partial cross section of the detection and decontamination system 10A similar to that of FIGS. 2A and 3. FIG. 4 depicts a portion of the surface 30; layer 34 and particles 40 are removed to illustrate the arrangement of the optics 40 and electrodes 36. Again, the optics 36 are positioned substantially perpendicular to and below the electrodes 32, although other arrangements are contemplated.

Figure 5:
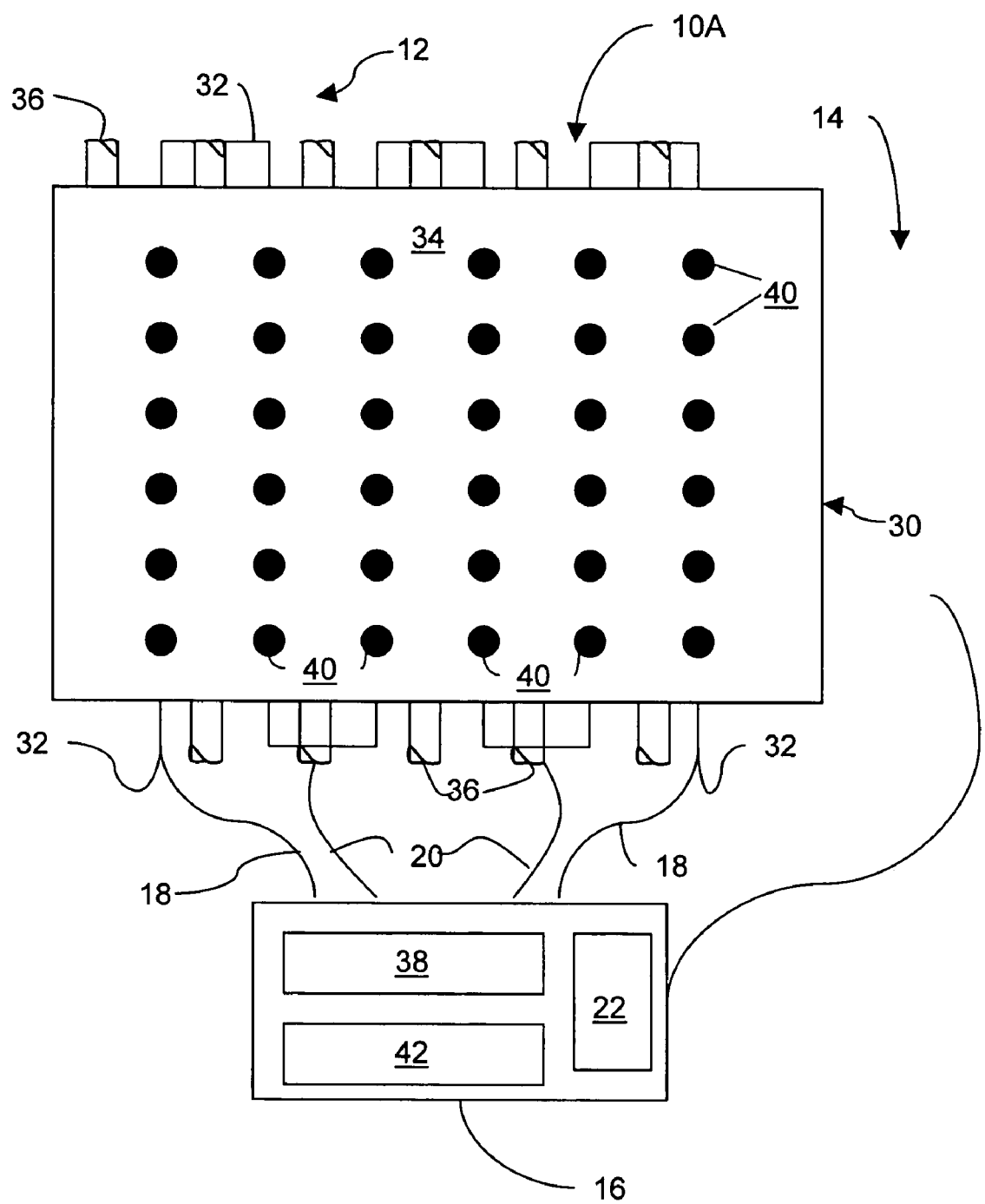
FIG. 5 depicts a plan view of another embodiment of the detection and decontamination system similar to that of FIG. 2A in accordance with one embodiment of the present invention.

FIG. 5 depicts a plan view of another embodiment of the detection and decontamination system 10A similar to that of FIGS. 2A and 3. In FIG. 5, the optics 36 are positioned substantially parallel to, and above, the electrodes 32, although again other arrangements are contemplated.

Figure 6:
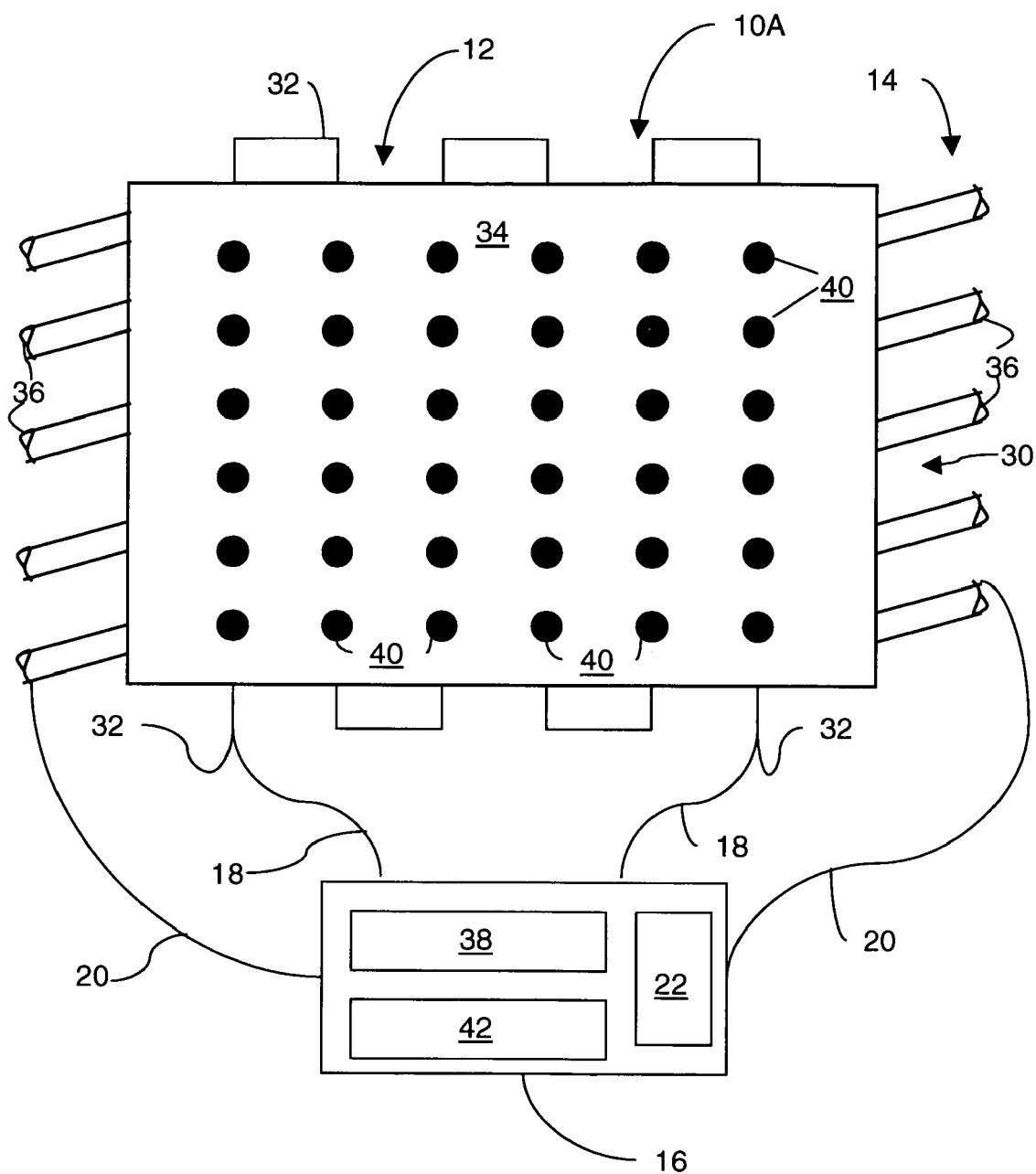
FIG. 6 depicts a plan view of another embodiment of the detection and decontamination system similar to that of FIG. 2A in accordance with one embodiment of the present invention.

FIG. 6 depicts a plan view of another embodiment of the detection and decontamination system 10A similar to that illustrated in FIGS. 2A and 3. FIG. 6 depicts the optics 36 positioned at a predetermined angle to the electrodes 32, although again, other arrangements are contemplated.

Figure 7:
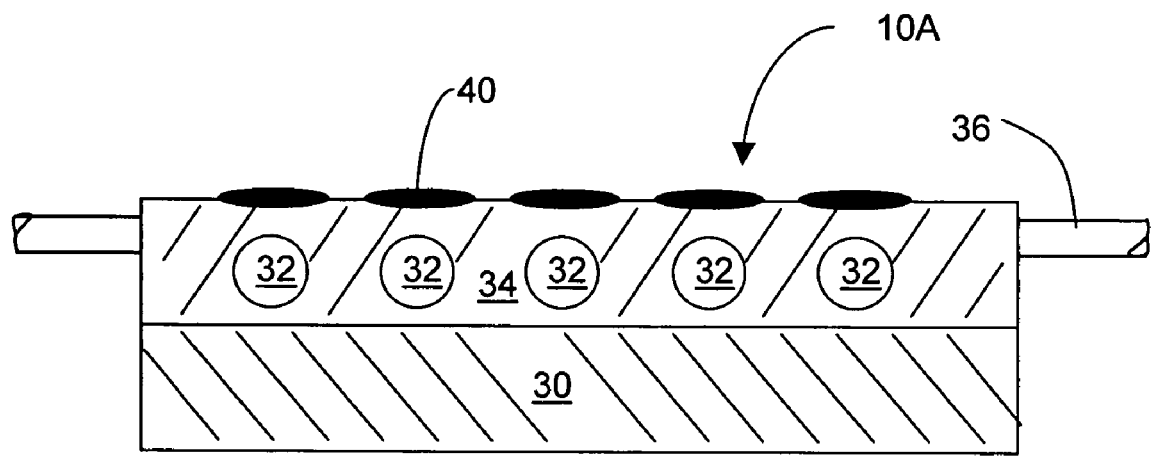
FIG. 7 depicts a side elevational view in partial cross section of the detection and decontamination system taken along line 7-7 of FIG. 2A accordance with one embodiment of the present invention.

FIG. 7 depicts a side elevational view of the system 10A and 10B in partial cross section in accordance with one embodiment of the present invention. FIG. 7 illustrates that at least one of the sensing and decontamination portions 12, 14 are embedded. Here, both the electrodes 32 and optics 36 are covered.

Figure 8:
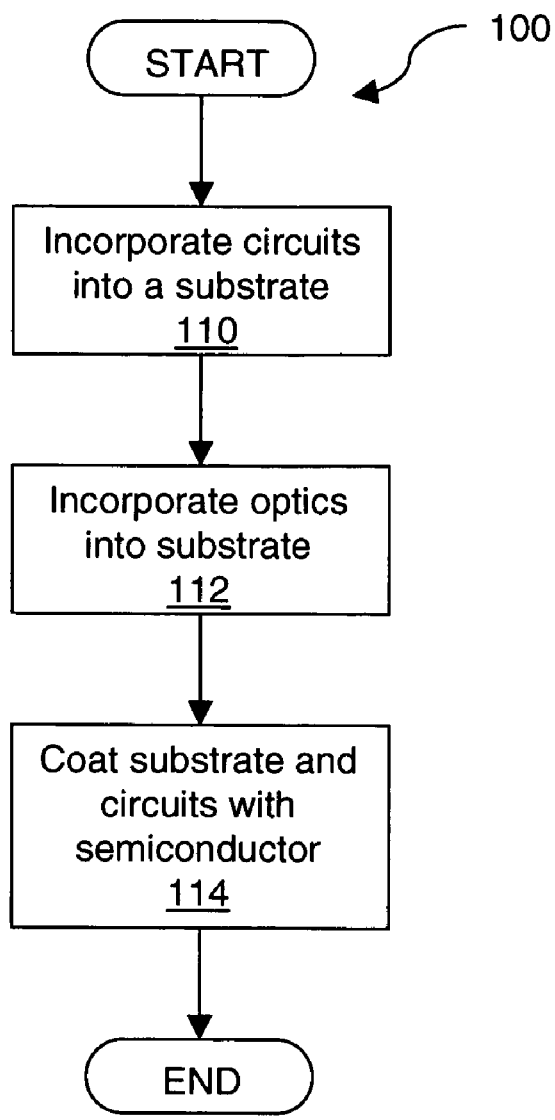
FIG. 8 depicts a high level flow diagram illustrating one method of forming or fabricating the detection and decontamination system illustrated in FIGS. 1-7 in accordance with one embodiment of the present invention.

FIG. 8 depicts a high level flow diagram illustrating one method, generally designated 100, of forming or fabricating the detecting/decontamination system illustrated in FIGS. 1-7 in accordance with one embodiment of the present invention. As illustrated, the method 100 comprises forming or fabricating the detecting/decontamination system including forming at least one "smart" surface adapted to detect contamination (chemical contamination for example) in near real-time and cleanse itself. This surface may be incorporated into glass, fabrics, painted surfaces, etc. Embodiments may be used by the military for fast response and decontamination situations. It could also be implemented in air cleansing systems.

Method 100 comprises incorporating one or more circuits into a substrate, designated block 110. In at least one embodiment, the substrate includes, but is not limited to, glass, ceramics, fabrics, painted surfaces, etc. Further, the one or more circuits comprise conductive films, microsensors, and/or mesh layers of microcircuits similar to that provided previously.

Method 100 further comprises incorporating one or more optics into the substrate, designated block 112. In at least one embodiment, the optics comprise scored (or unscored) fiber optic cables adapted to transmit energy (for example light having wavelengths more energetic than (equal to or exceeding) the bandgap energy of the semiconductor used include such sources as sunlight, xenon light, mercury lamps, etc.). The scored fiber optics are embedded in the substrate (including but not limited to glass, ceramics, fabrics, painted surfaces, etc). Unscored fiber optics, illumination from above the sensing/decontaminating surface, or various length fiber optics incorporated into the surface are also considered for the illumination source.

FIG. 8 further depicts method 100 comprising coating at least the substrate and circuits with a semiconductor. More specifically, the method 100 comprises coating at least one, but generally all, of the substrate, the circuits and the optics with the macroparticles, microparticles or nanoparticles of the semiconductor (a metal oxide semiconductor, $TiO_2$ for example, although other metal oxide semiconductors such as $SrTiO_3$, $ZnO$, $SrO$, $In_2O_3$, $GeO_2$, $Nb_2O_5$, $MoO_3$, $CeO_2$, $ThO_2$, $SnO_2$, $ZrO_2$, $VO_2$, $WO_3$, $CdS$, and $Fe_2O_3$ are contemplated). It is further contemplated that at least one of the substrate and circuits may be coated or covered by a mixture comprising different semiconductors, different sized particles of the same semiconductor or different sized particles of different semiconductors.

Figure 9:
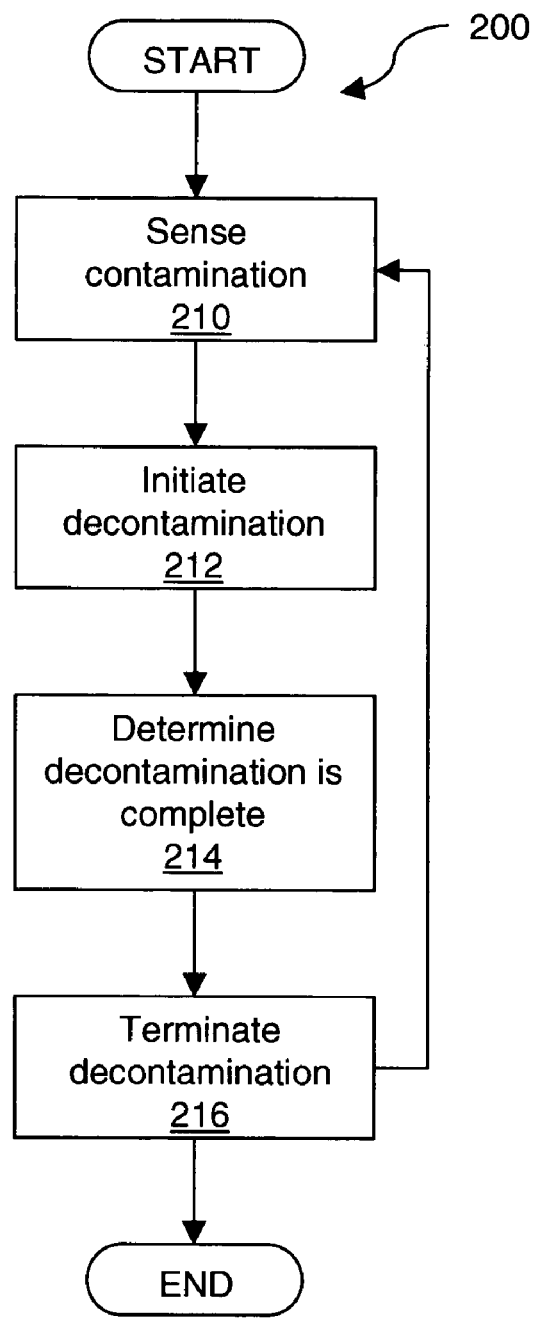
FIG. 9 depicts a high level flow diagram illustrating one method of detecting and decontaminating a contaminant in accordance with one embodiment of the present invention.

FIG. 9 depicts one method, designated 200, of detecting toxics and toxins on a surface (the smart surface) in near-real time, determining the concentration of the contaminants present, self-decontaminating the surface, and providing feedback information as to when decontamination process is complete. In the illustrated embodiment, method 200 comprises sensing a contaminant (toxics and/or toxins) physisorbed or chemisorbed onto one surface of the system for example (similar to that of one of the systems supra), designated block 210. Decontamination is initiated (self-decontamination for example), designated block 212. In one embodiment, decontamination comprises triggering the illumination of a light with energy greater than that of the semiconductor's bandgap energy at a source to initiate the semiconductor's decontamination reaction.

The method 200 further comprises determining if the decontamination is complete, designated block 214. In one embodiment, the method comprises providing feedback as to when the measured resistance and temperature matches the stored background resistance and temperature, which indicates that the contaminant has been oxidized or reduced (decontaminated) and desorbed from the surface. Finally, the decontamination is terminated, designated block 216. In one embodiment, the method 200 terminates after decontamination is terminated. However, it is contemplated that method 200 operates in a repetitive fashion.

Figure 10:
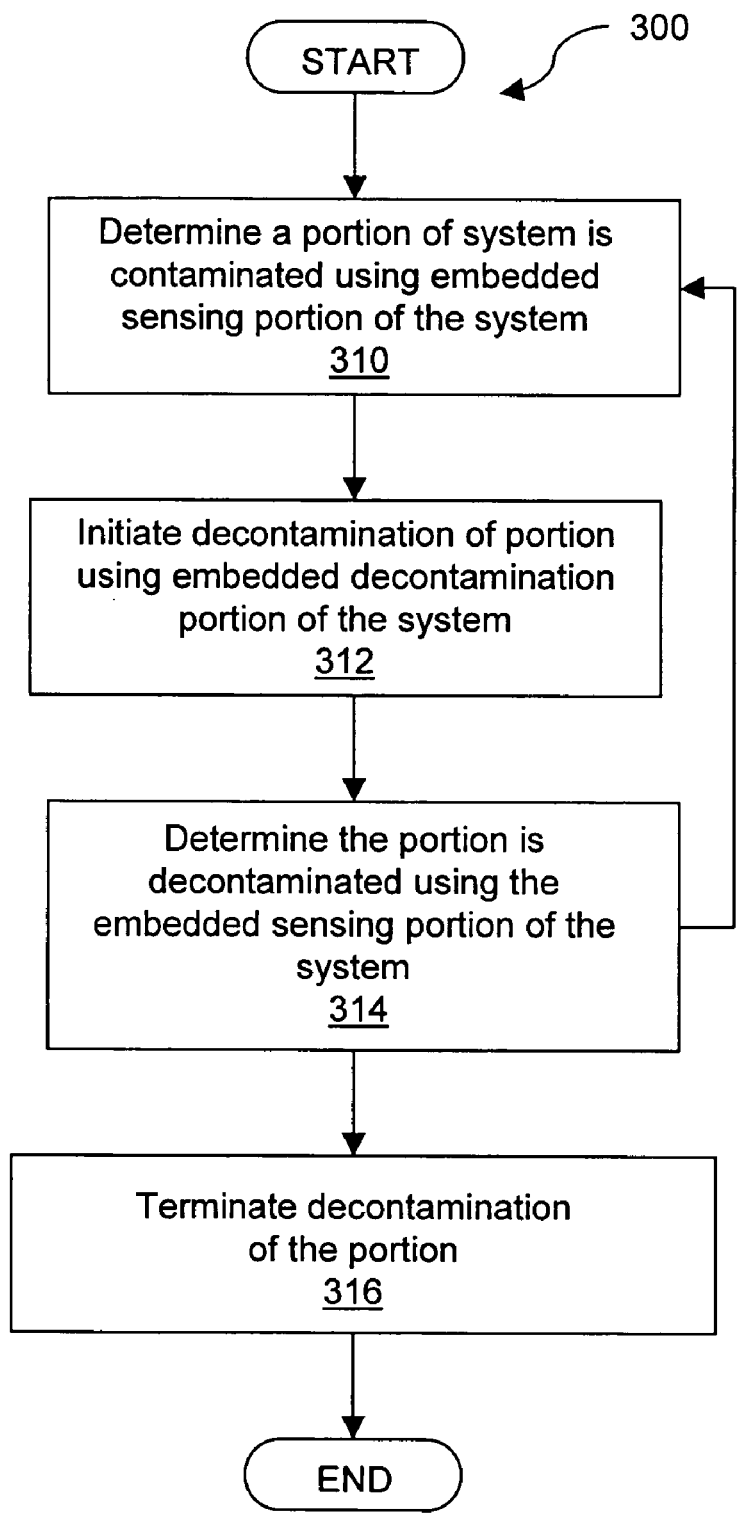
FIG. 10 depicts a detailed flow diagram illustrating one method of detecting and decontaminating a contaminant similar to that of FIG. 9 in accordance with one embodiment of the present invention.

FIG. 10 depicts one method, designated 300, of detecting toxics and toxins on a surface in near-real time, determining the concentration of the contaminants present, self-decontaminating the surface, and providing feedback information as to when the decontamination processes are complete. In the illustrated embodiment, method 300 comprises determining if a portion of the system is contaminated by contaminant, designated block 310. The method 300 uses an embedded sensing portion to determine if a contaminant has been physisorbed or chemisorbed onto one surface thereof.

Decontamination is initiated (self-decontamination for example) for at least a portion of the system using an embedded decontamination portion, designated block 312. In one embodiment, all the system surfaces are decontaminated. However, at least one embodiment is contemplated wherein the embedded decontamination portion only decontaminates that portion of the system that is contaminated.

The method 300 further comprises determining if the decontamination is complete, designated block 314. In this embodiment, the system uses the embedded sensing portion to provide feedback as to when the resistance matches the stored background resistance, which indicates that the contaminant has been oxidized or reduced (decontaminated) and desorbed from the surface. Finally, the decontamination is terminated, designated block 316. In one embodiment, the method 300 terminates after decontamination is terminated. However, it is contemplated that method 300 operates in a repetitive fashion.

Figure 11:
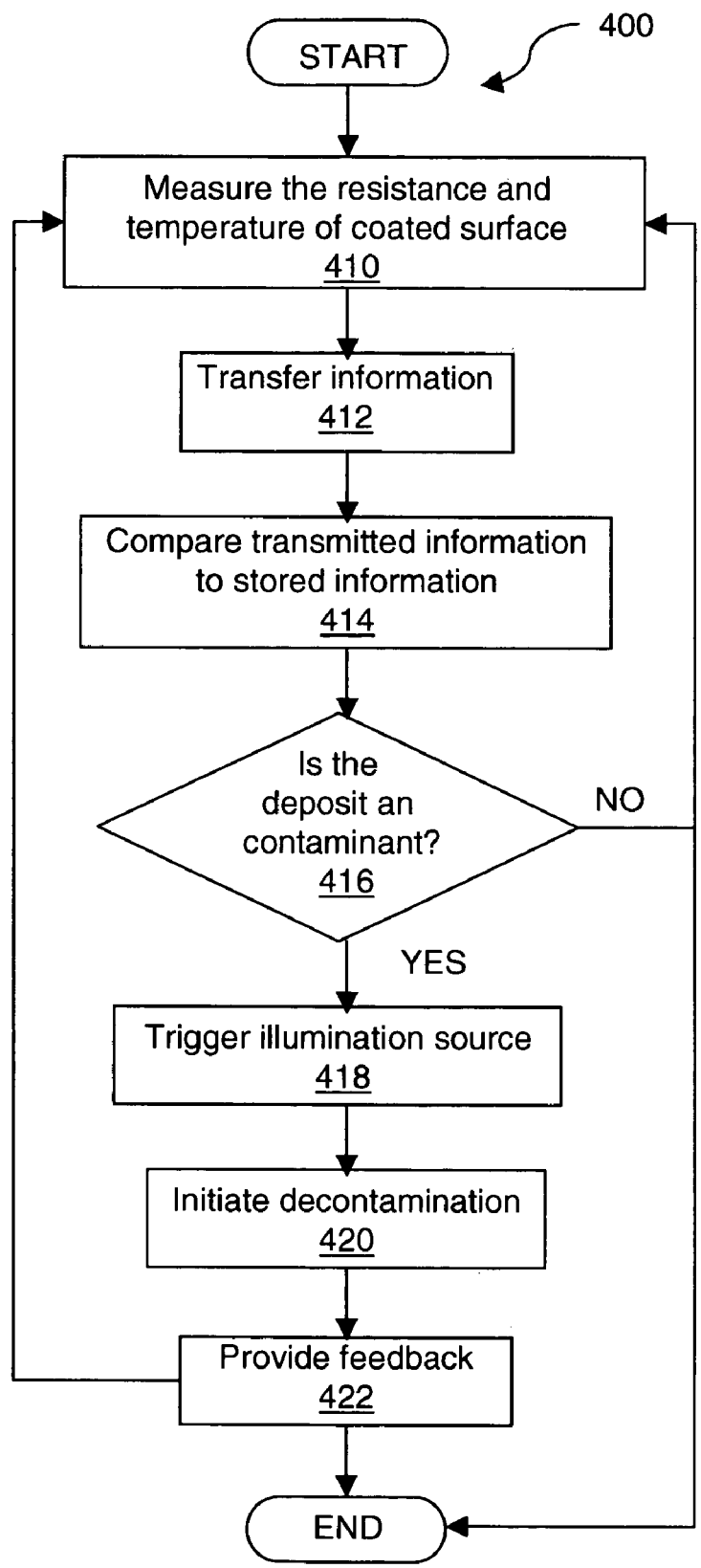
FIG. 11 depicts a detailed flow diagram illustrating one method of detecting and decontaminating a contaminant similar to that of FIGS. 9 and 10 in accordance with one embodiment of the present invention.

FIG. 11 depicts one method, designated 400, of detecting the presence of a deposit on a surface in near-real time, determining the concentration of the deposit, determining if the deposit is a contaminant, self-decontaminating the surface, and providing feedback information as to when the decontamination process is complete. In the illustrated embodiment, method 400 comprises measuring the resistance and temperature of at least one coated surface of the system, designated block 410. The method 400 uses an embedded sensing portion to measure the resistance and temperature. In one embodiment, the resistance and temperature are measured periodically. However, embodiments are contemplated in which the resistance and temperature are continuously measured.

The information (i.e., data representing the measured resistance and temperature) is transferred or transmitted to the controller, designated block 414. The controller compares the transmitted information to information stored therein (in a lookup table/signature library in near real-time) to determine if the deposit is a contaminant and the concentration of the deposit, designated block 414. In one embodiment, the information stored in the controller comprises the background resistance and temperatures of uncontaminated materials as a standard curve.

The system determines if the deposit is a contaminant or non-contaminant, designated diamond 416. Comparison of the information to signatures stored in the lookup table determines if the deposit is a contaminant or non-contaminant. If the deposit is a noncontaminant, method 400 may either terminate or measure resistance and temperature of the surface again in a repetitive fashion.

If the system determines that the information deems the sorbant is a contaminant, then the method 400 triggers an illumination source and initiates decontamination, designated blocks 418 and 420 respectively. The illumination is dispersed through at least a portion of the system, designated block 420. In one embodiment, the illumination source is dispersed using at least one fiber optic cable embedded in the system. The illumination source also can be positioned above the sensor/decontamination surface.

FIG. 11 further illustrates that the method 400 further comprises providing feedback, designated block 422. In one embodiment, the method provides feedback as to when the resistance matches the stored background resistance, which indicates that the contaminant has been oxidized or reduced (decontaminated) and desorbed from the surface.

Experimental Sensor Fabrication

Figure 12:
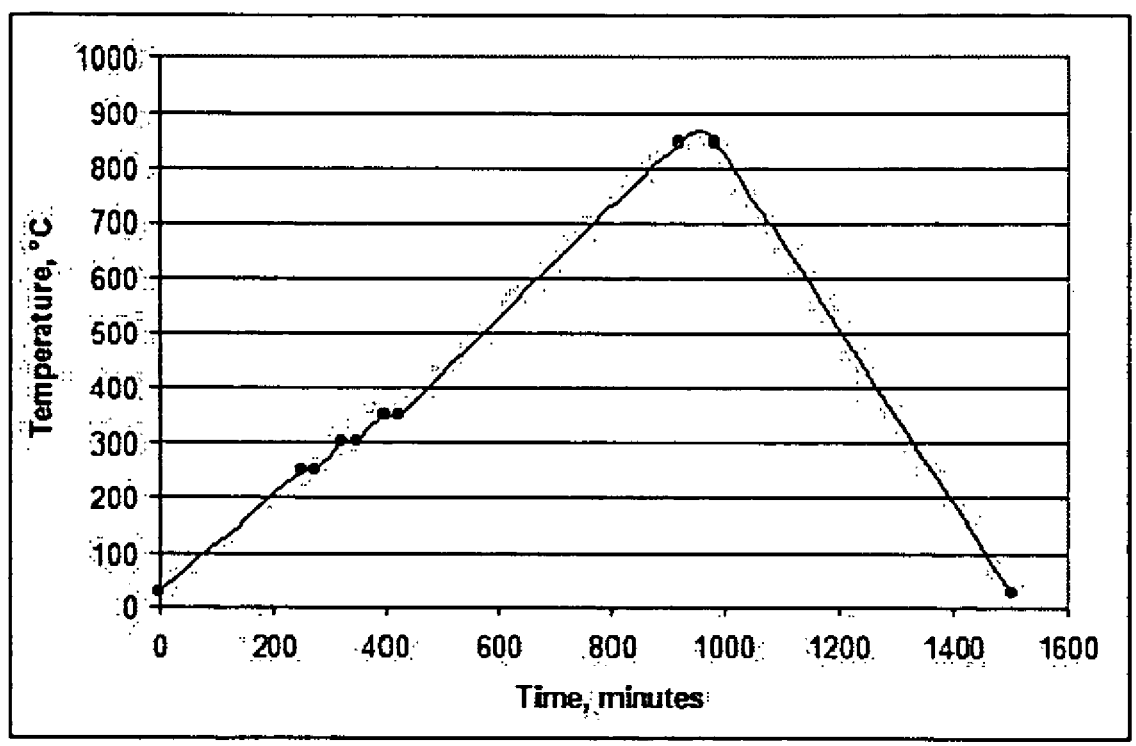
FIG. 12 depicts a schematic representation of the furnace firing profile for platinum electrodes.

An experimental sensor in accordance with one embodiment was fabricated by first depositing a metal electrode as a paste containing the metal in an organic vehicle on a substrate's surface. The metal electrode-substrate was air-dried and fired at about 825° C. to be certain that the organic vehicle was removed. The substrate was selected from the group consisting of alumina, $Al_2O_3$. The metal was selected from the group consisting of gold, platinum, and silver. FIG. 12 depicts a schematic representation of a furnace firing profile for platinum electrodes fabricated using this method. The electrodes were slowly heated to about 825° C. over a period of one hour, maintained at that temperature for more than an hour, and cooled to ambient temperature for approximately two hours.

Semiconductor metal oxide was subsequently screened on top and around the metal electrode as a paste via an organic vehicle. The metal oxide was selected from the group consisting of tin (IV) oxide, $SnO_2$; zinc oxide, $ZnO$; titanium (IV) oxide, $TiO_2$; cadmium sulfide, $CdS$; and zirconium oxide, $ZrO_2$. The entire sensor was air-dried and subsequently fired up to 350° C. for two hours, again to be certain the organic vehicle was removed. The metal electrode enables the metal oxide film to be attached to external equipment and monitored while chemical reactions take place on the metal oxide surfaces. The portions of the electrodes not covered by the metal oxide were connected to wire leads leading to a data acquisition and signal processing system.

Specifically, a $TiO_2$ gas microsensor was prepared by first depositing desired patterns of thick films (less than 5 µm) consisting of platinum (Heraeus Conductor Paste, Product LPI 11-4493) onto aluminum oxide, $Al_2O_3$ substrate using a pneumatic industrial thick-film screen printer (Presco Model 873 with Ikegami optics). After air-drying, the films were fired (in a Lindberg type 51524 furnace) according to the profile depicted in FIG. 12. After cooling, a deposit of anatase $TiO_2$ (Degussa P25) was placed as a thick film (5 µm) mixed with Heraeus vehicle RV-025, 1.0 grams of $TiO_2$ to 6.5 grams RV-025. Antase $TiO_2$ was used as opposed to rutile $TiO_2$ because the anatase form is more reactive.

MEASUREMENT EXAMPLE

Shielded electrical leads were connected to a $TiO_2$ sensor in a quartz reaction chamber. The sensor was positioned in the middle of the chamber. A rubber stopper covered in aluminum encased the leads and sealed the chamber. For the analysis of each gaseous organic moiety, the chamber was opened to the atmosphere and flushed with compressed zero chromatographic air for ten minutes at a rate greater than 10 liters per minute. The sensor was inserted into the quartz reaction chamber, sealed with the stopper, and placed into a reactor (Rayonet Photochemical Chamber Reactor RMR Model 600) containing eight ultraviolet (UV) lights producing 253.7 nanometer light, providing a quantum yield of 0.100 Einstein per minute.

A cyclic potential sweep was applied to the sensor from −5.00V to +5.00V producing a residual current curve. The system used to gather the $TiO_2$ sensor response data was composed of commercial-off the shelf hardware and proprietary voltammetry software. The system allowed complete control over the applied potential sweep and acquisition to capture photocatalytic responses and the concomitant electrical responses. A complete signature was captured for each experimental run. Either all of the voltammogram or the linear sweep section (negative potential to positive potential) was used for sensor evaluation.

TABLE 1 illustrates saturation concentrations of six different contaminant gases used in the experimental runs. The amount of each contaminant used was such that the volume around the sensor was saturated with the contaminant at the given ambient pressure and temperature.

TABLE 1

Concentrations[1] of contaminant gases

| Compound | Maximum concentration (ppm)[2] |
|---|---|
| Methylene Chloride, $CH_2Cl_2$ | 464,000 |
| Ethanol, $C_2H_6O$ | 59,00 |
| Benzene, $C_6H_6$ | 126,000 |
| Isopropanol, $C_3H_8O$ | 43,000 |
| Xylene, $C_8H_{10}$ | 13,000 |
| Acetone, $C_3H_6O$ | 285,000 |

Figure 13:
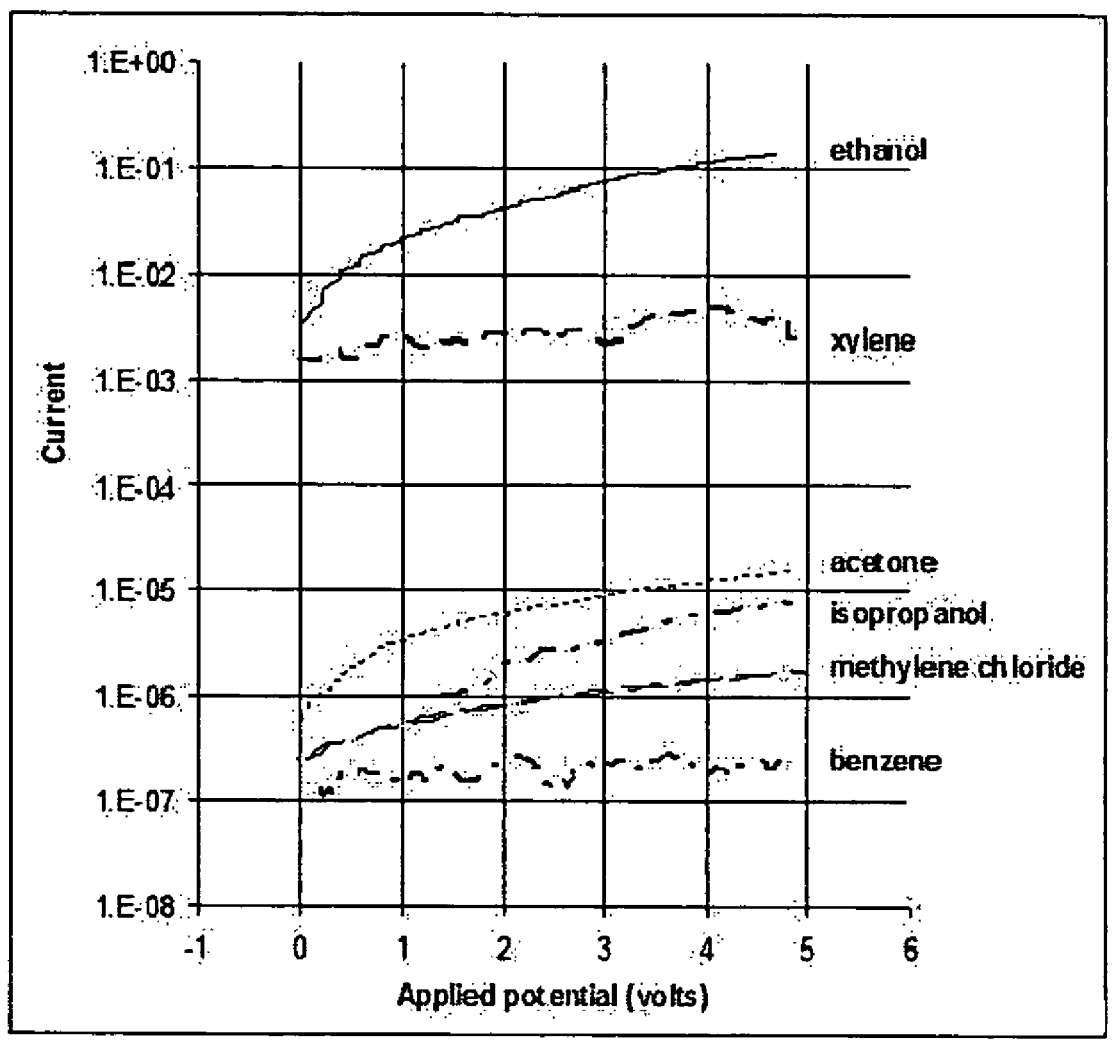
FIG. 13 depicts a schematic representation illustrating the linear sweep response of the $TiO_2$ sensor in accordance with one embodiment of the present invention.

[1]Satuation concentrations were calculated from contaminant vapor pressures
[2]ppmv is parts per million volume FIG. 13 depicts a schematic representation illustrating the linear sweep response of the $TiO_2$ sensor. In this figure, the linear sweep response is a plot of current in amperes versus applied potential difference in volts, to saturated concentrations of the six organic moieties provided in Table 1 in a zero chromatographic air atmosphere. Only one quadrant of the voltammogram is shown to simplify the response signal. Both the voltage and the current are direct. As may be seen in FIG. 13, distinct responses are obtained from the $TiO_2$ sensor as it is exposed to saturated concentrations of various constituents in air. Uniquely different responses are obtained for each contaminant as each contaminant, due to its different electronic and physical structure, has a different reaction with and effect upon the sensor's surface.

Figure 14:
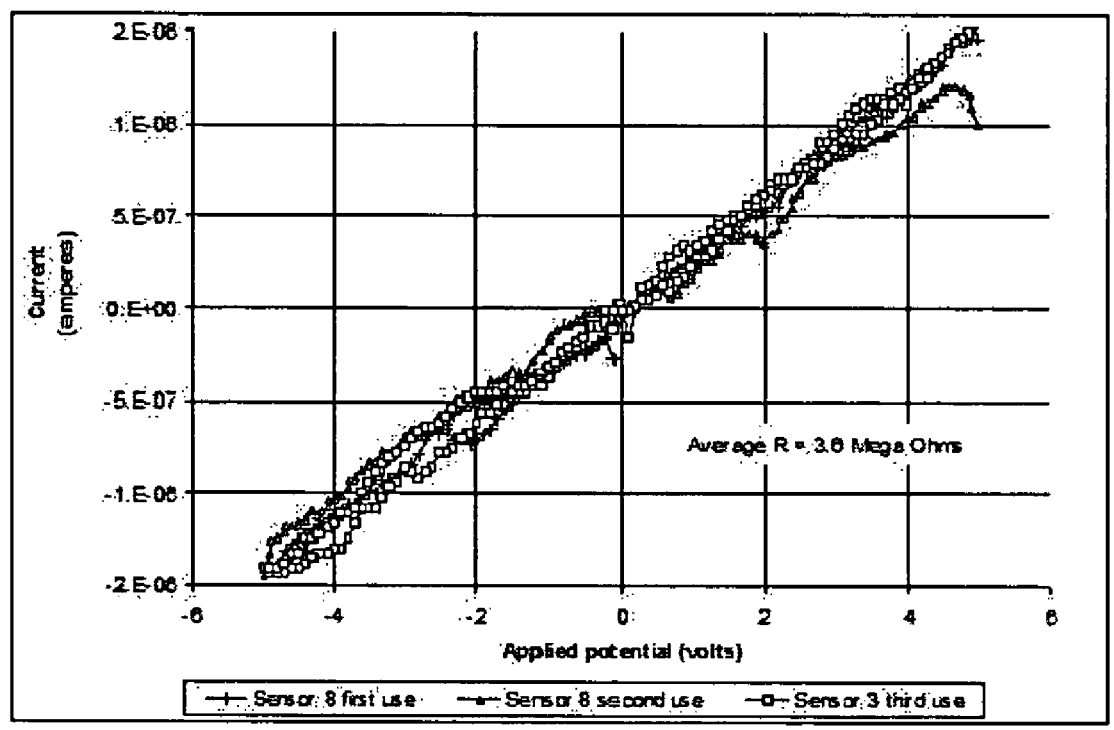
FIG. 14 depicts a schematic representation illustrating the response of two sensors in accordance with one embodiment of the present invention.

FIG. 14 depicts a schematic representation illustrating the response of two sensors, as a plot of current in amperes to applied potential difference in volts, to methylene chloride, $CH_2Cl_2$, in the presence of ultraviolet light. The curves depicted in FIG. 14 illustrate three responses: 1) the response of a newly fabricated sensor (designated sensor "8") to methylene chloride, 2) the response of the sensor 8 to methylene chloride a week after the initial test was performed, and 3) the response of a different sensor (designated "sensor 3") to methylene chloride. Sensor 8 had previously been used twice to detect isopropanol. As seen in FIG. 14, the three responses are essentially identical.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

The embodiment of the invention in which an exclusive property or privilege is claimed is defined as follows:

1. A system for identifying and making quantitative determinations with respect to deposits on a portion of the system, determining that the deposit is a contaminant, and decontaminating at least the portion of the system, the system comprising:
   a) a controller containing information about at least one contaminant;
   b) an embedded sensing portion monitoring an atmosphere above said sensing portion, wherein said atmosphere comprises air, the sensing portion communicating with at least said controller and adapted to detect a quantity of the deposits, the sensing portion comprising film layer on a surface and maintained at atmospheric pressure and temperature, wherein said deposit is physisorbed or chemisorbed directly from said atmosphere to said surface; and
   c) an embedded self-decontaminating portion triggered by the sensing portion and communicating with at least said controller to determine a resistance and temperature of the surface and adapted to decontaminate the portion of the system wherein the sensing portion and the self-decontaminating portion are substantially encapsulated within the surface; wherein said embedded sensing portion, and said self-decontaminating portion are integrally molded on said surface.

2. The system as recited in claim 1 wherein said controller includes a signature library storing data of at least one of a resistance and temperature of at least one non-contaminant.

3. The system as recited in claim 1 wherein said sensing and decontaminating portions are coupled to said controller using at least one connection.

4. The system as recited in claim 2 wherein said sensing portion comprises at least one electrode adapted to measure at least one of resistance and temperature of the deposit.

5. The system as recited in claim 4 wherein said controller is adapted to compare said measured at least one resistance and temperature with said stored at least one resistance and temperature to determine if the deposit is a contaminant.

6. The system as recited in claim 1 wherein said decontamination portion comprises at least one optic source adapted to provide light having energy greater than the bandgap energy of a semiconductor comprising the layer, thereby decontaminating at least the portion of the system.

7. The system as recited in claim 1 wherein at least a portion of the system is coated with a semiconductor material.

8. The system as recited in claim 7 wherein said decontamination portion comprises at least one optic adapted to provide light having energy equal to or exceeding said semiconductor's bandgap energy to decontaminate the portion of the system.

9. The system as recited in claim 7 wherein said semiconductor comprises a compound selected from the group consisting of $TiO_2$, $SrTiO_3$, $ZnO$, $SrO$, $In_2O_3$, $GeO_2$, $Nb_2O_5$, $MoO_3$, $CeO_2$, $ThO_2$, $SnO_2$, $ZrO_2$, $VO_2$, $WO_3$, $CdS$, and $Fe_2O_3$.

10. The system as recited in claim 7 wherein said sensing portion is adapted to measure a resistance and temperature of said semiconductor.

11. The system as recited in claim 1 wherein said controller activates or deactivates the sensor portion or the decontamination portion.

12. The system as recited in claim 1 wherein the sensing portion is exposed to an atmosphere containing organic contaminants wherein the controller contains at least one of a resistance and temperature of said at least organic contaminants.

13. The system as recited in claim 1 wherein the decontamination process continues on a feedback loop until said contaminant is decontaminated from the surface.

* * * * *